United States Patent [19]

Saari et al.

[11] 4,252,816
[45] Feb. 24, 1981

[54] TETRAHYDRO-1H-1,4-DIAZEPINO(1,7-A)BENZIMIDAZOLES USEFUL AS ANALGESIC AGENTS

[75] Inventors: Walfred S. Saari, Lansdale; Joel R. Huff, Gwynedd, both of Pa.

[73] Assignee: Merck & Co., Inc., Rahway, N.J.

[21] Appl. No.: 99,387

[22] Filed: Dec. 3, 1979

[51] Int. Cl.³ .................... A61K 31/55; C07D 487/04
[52] U.S. Cl. ........................... 424/273 B; 260/245.6; 548/330; 564/442; 564/443
[58] Field of Search ......................... 260/245.6, 245.5; 424/273 B

[56] References Cited

U.S. PATENT DOCUMENTS

| | | | |
|---|---|---|---|
| 4,081,542 | 3/1978 | Lumma, Jr. et al. | 424/250 |
| 4,082,844 | 4/1978 | Lumma, Jr. et al. | 424/250 |

FOREIGN PATENT DOCUMENTS 1492528  11/1977  United Kingdom ............... 424/250

OTHER PUBLICATIONS

Chem. Abs., vol. 87, 39362r—J. Chem. Soc., Perkin Trans I, 1977 (5), 478-483.

Primary Examiner—Alton D. Rollins
Attorney, Agent, or Firm—Raymond M. Speer; Mario A. Monaco

[57] ABSTRACT

Substituted tetrahydro-1H-1,4-diazepino[1,7-a]benzimidazoles of the formula:

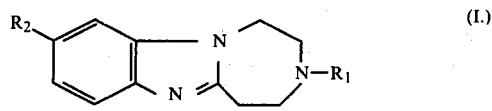

(I.)

and pharmaceutically acceptable salts thereof having thereapeutic activity as analgesic agents.

15 Claims, No Drawings

TETRAHYDRO-1H-1,4-DIAZEPINO(1,7-A)BENZIMIDAZOLES USEFUL AS ANALGESIC AGENTS

BACKGROUND OF THE INVENTION

1. Field of the Invention

The present invention is concerned with novel substituted 2,3,4,5-tetrahydro-1H-1,4-diazepino[1,7-a]benzimidazoles and pharmaceutically acceptable salts thereof which are useful as analgesic agents, to pharmaceutical compositions containing these compounds, and to methods of administering these compounds to an animal or human.

2. Brief Description of the Prior Art

British Pat. No. 1,492,528 and U.S. Pat. Nos. 4,081,542 and 4,082,844 all disclose piperazinylpyrazines having pharmacological activity as anorexic agents. Use of the compounds as analgesic agents is also indirectly suggested. However, the disclosures of these references do not teach or suggest the compounds of the present invention or their usefulness as analgesic agents.

SUMMARY OF THE INVENTION

The novel compounds of the present invention have the structural formula:

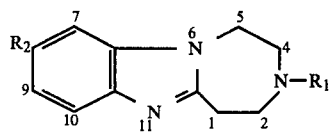

wherein:

$R_1$ is hydrogen; $C_{1-4}$ alkyl, for example n-propyl; or cyclopropylmethyl; and $R_2$ is hydrogen; halo, for example chloro or fluoro; $C_{1-4}$ alkyl, for example methyl; $C_{1-4}$ alkoxy, for example methoxy; hydroxy; or trifluoromethyl;

and pharmaceutically acceptable salts thereof.

The most preferred compounds of this class are:

8-chloro-2,3,4,5-tetrahydro-1H,-1,4-diazepino[1,7-a]benzimidazole 8-methoxy-2,3,4,5-tetrahydro-1H-1,4-diazepino[1,7-a]benzimidazole 3-n-propyl-8-chloro-2,3,4,5-tetrahydro-1H-1,4-diazepino[1,7-a]benzimidazole 3-cyclopropylmethyl-8-chloro-2,3,4,5-tetrahydro-1H-1,4-diazepino[1,7-a]benzimidazole Also included within the scope of the present invention are non-toxic pharmaceutically acceptable salts. For example, acid addition salts of the novel compounds are formed by mixing a solution of the compound with a solution of a pharmaceutically acceptable non-toxic acid such as hydrochloric acid, fumaric acid, maleic acid, succinic acid, carbonic acid, sulfuric acid, phosphoric acid, nitric acid, isethionic acid or the like.

The novel compounds of the present invention may be prepared by a process in which:

(1) a 4-substituted-2-(2-hydroxyethylamino)-aniline is reacted with β-alanine in the presence of an acid to effect ring closure and form a 1-(2-hydroxyethyl)-2-(2-aminoethyl)-6-substituted benzimidazole;

(2) the benzimidazole is reacted with di-t-butyl carbonate to form a 2-(2-t-butoxycarbonylaminoethyl) derivative of the benzimidazole;

(3) the product of (2) is reacted with p-toluenesulfonyl chloride to form a 1-(2-p-toluenesulfonyloxyethyl) derivative of the benzimidazole;

(4) the product of (3) is treated with trifluoroacetic acid followed by a carbonate solution in order to remove the t-butoxy protective group and to effect ring closure and form an 8-substituted-2,3,4,5-tetrahydro-1H-1,4-diazepino[1,7a]benzimidazole; and, optionally, (5) the product of (4) is treated with an $XR_1$ compound (where $R_1$ and $X$ have the same meaning as above) in order to form the 3-substituted compounds of the present invention.

The above reactions may be represented by the following diagram:

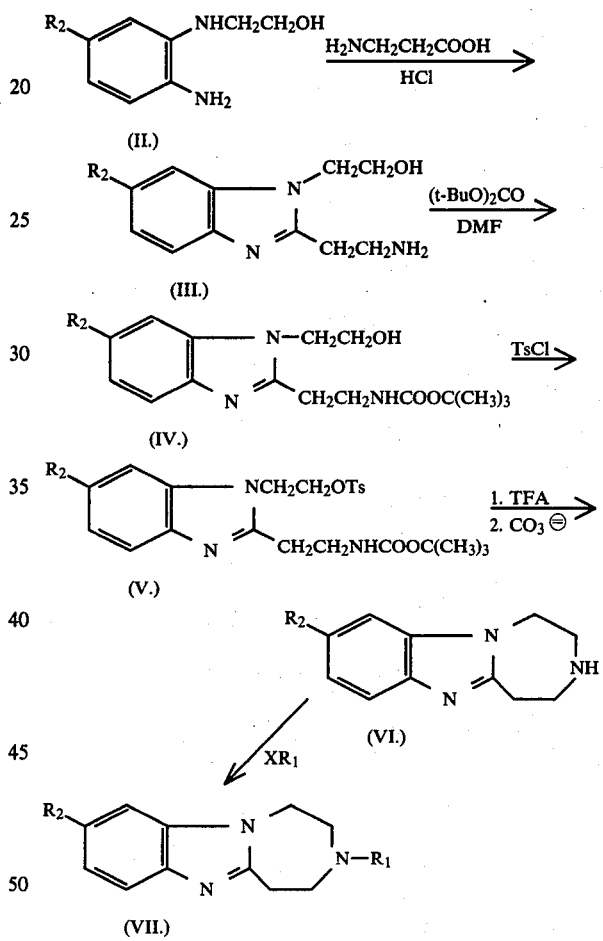

where X is a readily displaceable group, such as halo, tosyloxy, or mesyloxy.

A further embodiment of the present invention is a method of treating pain in patients in need of such treatment that comprises administering to such patients a therapeutically effective amount of a compound of the formula:

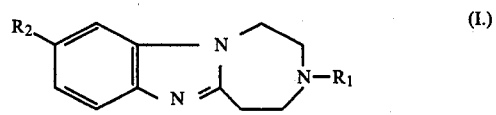

wherein $R_1$ and $R_2$ have the same meaning as above, and non-toxic pharmaceutically acceptable salts thereof.

In such administration for the treatment of pain, typically the dosage level ranges from about 0.1 to about 100 mg. per day of the active compounds of the present invention.

A still further embodiment of the present invention is a pharmaceutical composition comprising a pharmaceutical carrier and a therapeutically effective amount of a compound of the formula:

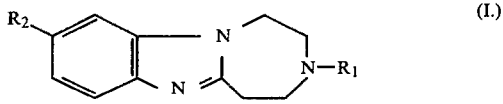

wherein $R_1$ and $R_2$ have the same meaning as above, and non-toxic pharmaceutically acceptable salts thereof.

The pharmaceutical composition may be in any art recognized form suitable for oral use, such as tablets, troches, lozenges, aqueous or oil suspensions, dispersible powders or granules, emulsions, hard or soft capsules, syrups, or elixirs. For intravenous, intramuscular, and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from about 0.1 to about 100 mg.

The following examples illustrate the present invention without, however, limiting the same.

EXAMPLE 1

8-chloro-2,3,4,5-tetrahydro-1H-1,4-diazepino[1,7-a]benzimidazole dihydrochloride

A.

1-(2-Hydroxyethyl)-2-(2-aminoethyl)-6-chlorobenzimidazole dihydrochloride hemihydrate A mixture of 9.7 g. (52 mmole) 2-(2-hydroxyethylamino)-4-chloroaniline, 6.9 g. (78 mmole) β-alanine, 46 ml. concentrated hydrochloric acid and 54 ml. of water is heated at reflux with stirring for 24 hrs. After cooling, the solution is concentrated, and made basic with 10% aqueous sodium hydroxide. Continuous liquid-liquid extraction of the aqueous solution with ethyl acetate affords 9.9 g. of the product, which is converted to it hydrochloride salt. The product has a m.p. of 196°–200° C. after recrystallization from methanol/ethyl acetate.

B.

1-(2-Hydroxyethyl)-2-(2-t-butoxycarbonylaminoethyl)-6-chlorobenzimidazole

To a slurry of 1.0 g (3.1 mmole) 1-(2-hydroxyethyl)-2-(2-aminoethyl)-6-chlorobenzimidazole dihydrochloride hemihydrate prepared in Step A. above in 15 ml. of dimethylformamide is added 0.66 g. (6.5 mmole) triethylamine, followed in 5 min. with 0.74 g. (3.4 mmole) of di-t-butyl carbonate. After stirring at room temperature for 3 hours, the reaction is diluted with 80 ml. of water and extracted with ethyl acetate. The organic layer is dried with calcium sulfate and concentrated to yield 1.0 g. of the desired material as a slightly yellow oil which crystallizes upon trituration with ethyl ether/hexane.

C.

1-(2-p-Toluenesulfonyloxyethyl)-2-(2-t-butoxycarbonylaminoethyl)-6-chlorobenzimidazole A solution of 1.5 g. (4.6 mmole) of 1-(2-hydroxyethyl)-2-(2-t-butoxycarbonylaminoethyl)-6-chlorobenzimidazole prepared in Step B. above and 1.0 g. (5.5 mmole) p-toluenesulfonyl chloride in 7.5 ml. of dry pyridine is heated at 50° C. for 2 hours. After cooling the reaction mixture is partitioned between dichloromethane and saturated sodium hydrogencarbonate solution. The organic extracts are dried with calcium sulfate and concentrated to remove solvent. The remaining pyridine is removed by azeotroping with toluene. The desired product, 1.6 g. (70%), is obtained as a crystalline solid.

D.

8-Chloro-2,3,4,5-tetrahydro-1H-1,4-diazepino[1,7-a]benzimidazole dihydrochloride 1.5 g. (3.0 mmole) of 1-(2-p-toluenesulfonyloxyethyl)-2-(2-t-butoxycarbonylaminoethyl)-6-chlorobenzimidazole prepared in Step C. above is dissolved in 20 ml. of trifluoroacetic acid (TFA) at 0° C. After stirring at that temperature for 1 hour, the TFA is removed in vacuo and the residue is dissolved in 100 ml. of 20% aqueous 2-propanol containing 3 g. of potassium carbonate. This mixture is refluxed 2 hours, cooled, and concentrated in vacuo. The solid obtained is partitioned between dichloromethane and water. After drying the organic phase with calcium sulfate, the solvent is evaporated to afford the product as a white solid. This solid is dissolved in 15 ml. of 2-propanol and acidified with ethanolic hydrochloric acid. A white crystalline solid separates which is filtered, washed with 2-propanol, and dried to yield 0.85 g. (96%) of the dihydrochloride salt: m.p. 318° C. (dec).

EXAMPLE 2

3-Propyl-8-Chloro-2,3,4,5-tetrahydro-1H-1,4-diazepino[1,7-a]benzimidazole dihydrochloride A solution of 1.1 g. (5 mmole) of 8-chloro-2,3,4,5-tetrahydro-1H-1,4-diazepino[17-a]benzimidazole prepared in Example 1 above, 0.85 g. (5 mmole) 1-iodopropane, and 0.75 g. (7.5 mmole) of sodium carbonate in 100 ml. of 95% ethanol is refluxed 72 hours. After removing the solvent in vacuo, the residue is chromatographed over silica gel, eluting with hexane/chloroform saturated with ammonia (1:4). The product obtained is dissolved in absolute ethanol and acidified with ethanolic hydrochloric acid. The crystals which separate are filtered and dried to afford 0.41 g. (25%) of the dihydrochloride salt: m.p. 271°–274° C.

EXAMPLE 3

3-Cyclopropylmethyl-8-chloro-2,3,4,5-tetrahydro-1H-1,4-diazepino[1,7a]benzimidazole dihydrochloride Using cyclopropylmethyl bromide as the alkylating agent in the procedure described above in Example 2, the product was obtained (32%) as a white crystalline solid: m.p. 266°–269° C.

EXAMPLE 4

Preparation of Capsule Dosage Form

| Ingredient | Amount (Mg. per capsule) |
| --- | --- |
| 8-Chloro-2,3,4,5-tetrahydro-1H-1,4-diazepino[1,7a]benzimidazole dihydrochloride | 6 |
| Starch | 87 |
| Magnesium stearate 7 | |

The active ingredient, starch and magnesium stearate are blended together. The mixture is used to fill hard shell capsules of a suitable size at a weight of 100 mg. per capsule.

EXAMPLE 5

Preparation of Tablet Dosage Form

| Ingredient | Amount (Mg. per capsule) |
| --- | --- |
| 8-Methoxy-2,3,4,5-tetrahydro-1H-1,4-diazepino[1,7-a]benzimidazole dihydrochloride hemihydrate | 12 |
| Lactose | 200 |
| Corn Starch (for mix) | 50 |
| Corn Starch (for paste) | 50 |
| Magnesium stearate | 6 |

The active ingredient, lactose and corn starch (for mix) are blended together. The corn starch (for paste) is suspended in water at a ratio of 10 g. of corn starch per 80 ml. of water and heated with stirring to form a paste. This paste is then used to granulate the mixted powders. The wet granules are passed through a No. 8 screen and dried at 120° C. The dry granules are passed through a No. 16 screen. The mixture is lubricated with magnesium stearate and compressed into tablets in a suitable tableting machine. Each tablet contains 12 mg. of active ingredient.

What is claimed is:

1. A compound of the formula:

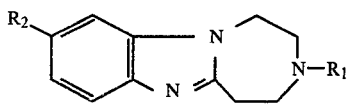

(I.)

wherein:

$R_1$ is hydrogen; $C_{1-4}$ alkyl; or cyclopropylmethyl; and
$R_2$ is hydrogen; halo; $C_{1-4}$ alkyl; $C_{1-4}$ alkoxy; hydroxy; or trifluoromethyl;
and a non-toxic pharmaceutically acceptable salt thereof.

2. A compound as in claim 1 wherein the compound is 8-chloro-2,3,4,5-tetrahydro-1H-1,4-diazepino[1,7-a]benzimidazole.

3. A compound as in claim 1 wherein the compound is 8-methoxy-2,3,4,5-tetrahydro-1H-1,4-diazepino[1,7-a]benzimidazole.

4. A compound as in claim 1 wherein the compound is 3-n-propyl-8-chloro-2,3,4,5-tetrahydro-1H-1,4-diazepino[1,7-a]benzimidazole.

5. A compound as in claim 1 wherein the compound is 3-cyclopropylmethyl-8-chloro-2,3,4,5-tetrahydro-1H-1,4-diazepino[1,7-a]benzimidazole.

6. A method of treating pain in a patient in need of such treatment comprising the administration to such a patient of a therapeutically effective amount of a compound of the formula:

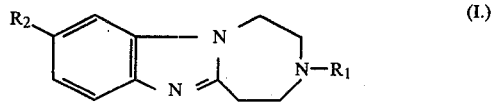

(I.)

wherein:

$R_1$ is hydrogen; $C_{1-4}$ alkyl; or cyclopropylmethyl; and
$R_2$ is hydrogen; halo; $C_{1-4}$ alkyl; $C_{1-4}$ alkoxy; hydroxy; or trifluoromethyl;
and a non-toxic pharmaceutically acceptable salt thereof.

7. A method as in claim 6 wherein the compound is 8-chloro-2,3,4,5-tetrahydro-1H-1,4-diazepino[1,7-a]benzimidazole.

8. A method as in claim 6 wherein the compound is 8-methoxy-2,3,4,5-tetrahydro-1H-14-diazepino[1,7-a]benzimidazole.

9. A method as in claim 6 wherein the compound is 3-n-propyl-8-chloro-2,3,4,5-tetrahydro-1H-1,4-diazepino[1,7-a]benzimidazole.

10. A method as in claim 6 wherein the compound is 3-cyclopropylmethyl-8-chloro-2,3,4,5-tetrahydro-1H-1,4-diazepino[1,7-a]benzimidazole.

11. A pharmaceutical composition for treating pain consisting essentially of a pharmaceutical carrier and a therapeutically effective amount of a compound of the formula:

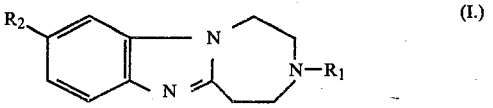

(I.)

wherein:

$R_1$ is hydrogen; $C_{1-4}$ alkyl; or cyclopropylmethyl; and
$R_2$ is hydrogen; halo; $C_{1-4}$ alkyl; $C_{1-4}$ alkoxy; hydroxy; and trifluoromethyl;
and a non-toxic pharmaceutically acceptable salt thereof.

12. A pharmaceutical composition as in claim 11 wherein the compound is 8-chloro-2,3,4,5-tetrahydro-1H-1,4-diazepino[1,7-a]benzimidazole.

13. A pharmaceutical composition as in claim 11 wherein the compound is 8-methoxy-2,3,4,5-tetrahydro-1H-1,4-diazepino[1,7-a]benzimidazole.

14. A pharmaceutical composition as in claim 11 wherein the compound is 3-n-propyl-8-chloro-2,3,4,5-tetrahydro-1H-1,4-diazepino[1,7-a]benzimidazole.

15. A pharmaceutical composition as in claim 11 wherein the compound is 3-cyclopropylmethyl-8-chloro-2,3,4,5-tetrahydro-1H-1,4-diazepino[1,7-a]benzimidazole.

* * * * *